(12) United States Patent
Johnson

(10) Patent No.: US 6,395,799 B1
(45) Date of Patent: May 28, 2002

(54) ELECTROMAGNETIC AND MECHANICAL WAVE ENERGY TREATMENTS OF UHMWPE

(75) Inventor: Russell A. Johnson, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/506,977

(22) Filed: Feb. 21, 2000

(51) Int. Cl.$^7$ .................................................. C08F 2/46
(52) U.S. Cl. ....................... 522/161; 522/157; 522/150; 522/3; 204/157.15
(58) Field of Search ................................. 522/150, 157, 522/161, 3; 264/232, 234, 235, 236, 237, 407, 410; 204/157.15

(56) References Cited

U.S. PATENT DOCUMENTS

| | | | |
|---|---|---|---|
| 4,055,862 A | | 11/1977 | Farling |
| 4,508,606 A | | 4/1985 | Andrade et al. |
| 4,586,995 A | | 5/1986 | Randall et al. |
| 4,587,163 A | | 5/1986 | Zachariades |
| 5,030,402 A | | 7/1991 | Zachariades |
| 5,037,928 A | | 8/1991 | Li et al. |
| 5,037,938 A | | 8/1991 | Brewbaker et al. |
| 5,047,446 A | | 9/1991 | DeNicola, Jr. |
| 5,079,283 A | * | 1/1992 | Burrditt et al. ................ 524/94 |
| 5,160,464 A | | 11/1992 | Ward et al. |
| 5,414,049 A | | 5/1995 | Sun et al. |
| 5,449,745 A | | 9/1995 | Sun et al. |
| 5,508,319 A | | 4/1996 | DeNicola, Jr. et al. |
| 5,543,471 A | | 8/1996 | Sun et al. |
| 5,650,485 A | | 7/1997 | Sun et al. |
| 5,728,748 A | | 3/1998 | Sun et al. |
| 5,814,266 A | * | 9/1998 | Pienkowski et al. ........ 264/443 |
| 5,879,400 A | * | 3/1999 | Merril et al. ................ 526/352 |
| 6,017,975 A | * | 1/2000 | Saum et al. ................. 522/161 |
| 6,165,220 A | * | 12/2000 | McKellop et al. .......... 128/898 |
| 6,228,900 B1 | * | 5/2001 | Shen et al. .................. 522/153 |
| 6,242,507 B1 | * | 6/2001 | Suam et al. ................. 522/161 |
| 6,245,276 B1 | * | 6/2001 | McNutly et al. ............ 264/322 |

FOREIGN PATENT DOCUMENTS

| | | |
|---|---|---|
| EP | 0722973 | 7/1996 |
| EP | 0729981 | 9/1996 |
| EP | 0737481 | 10/1996 |
| WO | 9521212 | 8/1995 |
| WO | 9729787 | 8/1997 |
| WO | 9729793 | 8/1997 |
| WO | 9801085 | 1/1998 |

OTHER PUBLICATIONS

Livingston et al., Trans. ORS, 22, 141–24, 1997.
Bloebaum et al., Clin. Orthop. 269, 120–127, 1991.
Polineni, V. K. et al., J 44$^{th}$ Annual ORS, 49, 1998.
Hamilton, J. V. et al., Scientific Exhibit, 64$^{th}$ AAOS Meeting, Feb. 1997.
Hamilton, J. V. et al., Trans 43$^{rd}$ ORS, 782, 1997.
Oonishi, H. et al., Radiat. Phys. Chem., 39(6), 495, 1992.
Oonishi, H. et al., Mat. Sci:Materials in Medicine, 7, 753–63, 1996.
Oonishi, H. et al., Mat. Sci: Materials in Medicine, 8, 11–18, 1997.
Oka, M. et al., "Wear–resistant properties of newly improved UHMPWE," Trans. 5$^{th}$ World Biomaterials Congress, 520, 1966.
Sun, D.C. et al., "Development of Stabilized UHMWPE Implants with Improved Oxidation Resistance via Crosslinking," Scientific Exhibit 63$^{rd}$ AAOS Meeting, Feb. 1996.

* cited by examiner

*Primary Examiner*—James J. Seidleck
*Assistant Examiner*—Sanza L. McClendon
(74) *Attorney, Agent, or Firm*—Fulbright & Jaworski L.L.P.

(57) ABSTRACT

A process for reducing or quenching free radical concentration in irradiated ultra high molecular weight polyethylene (UHMWPE) using electromagnetic or mechanical wave energy.

12 Claims, 6 Drawing Sheets

ELECTROMAGNETIC AND MECHANICAL WAVE ENERGY TREATMENTS OF UHMWPE

FIELD OF THE INVENTION

The present invention relates to a process for reducing or quenching free radical concentration in irradiated ultra high molecular weight polyethylene (UHMWPE). More particularly, the present invention relates to rapid quenching of free radicals to avoid long term oxidative degradation in irradiated cross-linked ultra high molecular weight polyethylene used to construct orthopedic implants.

BACKGROUND OF THE INVENTION

The replacement of destroyed or damaged human joints is one of the greatest achievements of Twentieth Century orthopedic surgery. However, total joint prosthesis, composed of various combinations of metal, ceramic, and polymeric components, continue to suffer from limited service lives.

UHMWPE is commonly used as an articulating, load-bearing surface in total joint arthoplasty. In the last decade, however, it has become apparent that wear debris from UHMWPE components may be a primary contributor to osteolysis, loosening and eventual failure of prosthetic joints. With steady increases in human life expectancy, there is a driving need to significantly increase the effective lifetime of a single implant. A desire to use prosthetic implants in younger patients is another strong incentive for improving the wear resistance of UHMWPE. As indicated below, the present invention discloses a process to improve long term wear characteristics of prosthetic implants made with UHMWPE.

When a human joint is destroyed or damaged by disease or injury, surgical replacement (arthoplasty) is normally required. A total joint replacement includes components that simulate a natural human joint, typically:

(a) a more-or-less spherical ceramic or metal ball, often made of cobalt chromium alloy;

(b) attachment of a "stem", which is generally implanted into the core of the adjacent long bone; and (c) a hemispherical socket which takes the place of the acetabular cup and retains the spherical ball. This hemispherical joint typically is a metal cup affixed into the joint socket by mechanical attachments and "lie" with UHMWPE. In this way, the ball can rotate within the socket, and the stem, via the ball, can pivot and articulate.

One of the difficulties in constructing any device for implantation into the human body is the need to avoid adverse immune responses. The probability of a severe immune response is reduced when certain synthetic materials are used. For example, synthetic UHMWPE implants have minimal immunogenicity problems. However, the wear and breakdown of the UHMWPE components are known in the art to cause immunology-related problems.

Histologic studies have demonstrated that wear of UHMWPE from orthopedic inserts leads to several problems. First, tissue surrounding implants constructed with UHMWPE has been shown to contain extremely small particles of UHMWPE which range from sub-micron to a few microns in size. While large particles of UHMWPE appear to be tolerated by the body, as is the intact solid wall of the UHMWPE implant, the body apparently does not tolerate smaller particles of UHMWPE. In fact, the small particles of UHMWPE can cause powerful histiocytic reactions by which the body unsuccessfully attempts to eliminate the foreign material. Agents released during this process attack neighboring bone to cause "wear debris" induced osteolysis. This in turn leads to loss of fixation and loosening of the prosthesis due to "remodeling" of the bone. The breakdown of UHMWPE during wear which leads to these adverse biological problems, can be due, in part, to degradation of polymer chains resulting from chemical oxidation of free radicals.

Numerous techniques have been proposed to improve wear resistance of UHMWPE in orthopedic implants. In these instances, however, many of the new versions of articulating polymers have generally failed to demonstrate significant reduction in wear and often prove to be inferior to conventional polyethylene. Recent attempts at improving wear properties of UHMWPE use special pressure/temperature processing techniques, surface treatments, formation of composites with high modulus fibers, and cross-linking via ionizing irradiation or chemical agents. Some of these attempts are summarized below.

1. Temperature/Pressure Treatments

Special thermal and pressure treatments have been used to increase physical performance and wear resistance of UHMWPE (e.g., U.S. Pat. Nos. 5,037,928 and 5,037,938). For example, "Hipping" (Hot Isostatic Pressing), produces material alleged to comprise fewer fusion defects, increased crystallinity, density, stiffness, hardness, yield strength and resistance to creep, oxidation, and fatigue. Clinical studies, however, indicate that "Hipping" treated UHMWPE may possess inferior wear resistance in comparison to conventional UHMWPE. The inferior wear resistance being due to increased stiffness which leads to increased contact stresses during articulation (Livingston et al., Trans. ORS, 22, 141–24, 1997).

Post-consolidation temperature and pressure treatment, such as solid phase compression molding (Zachariades, U.S. Pat. No. 5,030,402), have also been attempted. Zachariades utilized solid state processing to further consolidate and orient UHMWPE chains. Resistance to wear in orthopedic implants, however, was not improved.

2. Surface Treatments

Focusing upon the surface of UHMWPE components, attempts have been made to decrease wear by increasing smoothness and/or lubricity of the UHMWPE components surface. A group from Howmedica used a heat pressing technique to melt the articulating surface and remove machine marks from the surface of UHMWPE components such that the "wearing in" of rough machine marks could be avoided. This modification, however, resulted in delimination and high wear due to the fact that high articulation-induced stresses were located in regions where there was a sharp transition in crystalline morphology (Bloebaum et al., Clin. Orthop. 269, 120–127, 1991).

Andrade et al. (U.S. Pat. No. 4,508,606) suggested oxidizing the surface of a wet hydrophobic polymer surface to reduce sliding friction. The preferred means included applying a radio frequency glow discharge to the surface. With this technique, surface chemistries were altered by changing the time of gas plasma exposure and by altering the gas composition. The invention was proposed for the treatment of catheters to decrease surface friction properties while in a wet state. Similarly, Farrar (World Patent Application No. WO 95 212212) proposed using gas plasma treatments to cross-link the surface of UHMWPE and, thereby, increase its wear resistance. None of the plasma treatments, however, were practical because any perceived benefit would most likely wear away with articulation.

3. Composites

Because creep may be a contributor to UHMWPE wear, investigators have also included high modulus fibers in polyethylene matrices to reduce plastic deformation. (U.S. Pat. No. 4,055,862.) developed a "poly-to-carbon polyethylene composite" which failed significantly via delimination. Recently, Howmedica reported that a PET/carbon fiber composite exhibited 99% less hip simulated wear than conventional polyethylene over ten million cycles. (Polineni, V. K. et al., J. $44^{th}$ Annual ORS, 49, 1998.)

4. Cross-Linking

A. Ionizing Radiation Induced Cross-Linking

In the absence of oxygen, the predominant effect of ionizing radiation on UHMWPE is cross-linking. Cross-linking of UHMWPE forms covalent bonds between polymer chains which inhibit cold flow (creep) of individual polymer chains. Free radicals formed during irradiation, however, can exist indefinitely if termination by cross-linking or other forms of recombination do not occur. Furthermore, reacted intermediates are continuously formed and decayed. Exposure of these free radical species at any time (e.g., during irradiation, shelf-aging, or in vivo aging) to molecular oxygen or any other reactive oxidizing agent can result in their oxidation. Extensive oxidation leads to a reduction in molecular weight, and subsequent changes in physical properties, including wear resistance.

To reduce oxidation after gamma sterilization, some orthopedic manufacturers have implemented techniques to irradiate their materials under conditions that encourage cross-linking and reduce oxidation. These techniques include use of inert gas atmospheres during all stages of processing, use of vacuum packaging, and post sterilization thermal treatments. Specific examples of these techniques are given below.

Howmedica has developed various means for reducing UHMWPE oxidation associated with processing, i.e., the continual use of an inert gas during processing (see U.S. Pat. Nos. 5,728,748; 5,650,485; 5,543,471; 5,414,049; and 5,449,745). These patents also describe thermal annealing of the polymer to reduce or eliminate free radicals. The annealing temperature which is claimed (room temperature to 135° C.), however, avoids complete melting of UHMWPE.

Johnson & Johnson has disclosed in a European patent application (EP 0737481 A1 ) a vacuum packaging method with subsequent irradiation sterilization to promote cross-linking and reduce short- and long-term oxidative degradation. The packaging environment can contain an inert gas and/or hydrogen to "quench" free radicals. The cross-linking/sterilization method is claimed to enhance UHMWPE wear resistance (Hamilton, J. V. et al., Scientific Exhibit, $64^{th}$ AAOS Meeting, February 1997; Hamilton, J. V. et al., Trans $43^{rd}$ ORS, 782, 1997.).

Biomet's World Patent Application No. 97/29787 discloses the gamma irradiation of a prosthetic component in an oxygen resistant container partially filled with a gas capable of combining with free radicals (e.g., hydrogen).

Oonishi/Mizuho Medical Company-Japan and other investigators from Mizuho Medical Company began cross-linking PE (polyethylene) by gamma irradiation in 1971 for their SOM hip implants. Since then, they have studied the effect of a wide range of sterilization doses up to 1,000 Mrad on the mechanical, thermal, and wear properties of UHMWPE. They have also studied the effects of different interface materials on wear and found that alumina or zirconia heads on 200 Mrad irradiated UHMWPE liners produced the lowest wear rates (Oonishi, H. et al., Radiat. Phys. Chem., 39(6), 495, 1992; Oonishi, H. et al., Mat. Sci: Materials in Medicine, 7, 753–63, 1966; Oonishi, H. et al., J. Mat. Sci: Materials in Medicine, 8, 11–18, 1997).

Massachusetts General Hospital/Massachusetts Institute of Technology (MGH/MIT) has used irradiation (especially e-beam) treatments to cross-link UHMWPE. These treatments reduced simulator wear rates of hip components by 80 to 95% in comparison to non-sterilized controls (see, e.g., World Patent Application 97/29793). This technology enables UHMWPE to be cross-linked to a high degree; however, the degree of cross-linking is dependent upon whether the irradiated UHMWPE is in a solid or molten state.

Orthopaedic Hospital/University of Southern California has disclosed patent applications which seek to increase the wear resistance of UHMWPE hip components using irradiation followed by thermal treatment, such as remelting or annealing (World Patent Application WO 98/01085). Using this method, UHMWPE cross-linking was optimized such that the physical properties were above ASTM limits.

BMG's European Application (EP 0729981 A1) discloses a unique processing method for decreasing friction and abrasive wear of UHMWPE used in artificial joints. The method involves irradiating UHMWPE at a low dose to introduce a small number of cross-linking points. Irradiation is followed by uniaxial compression of melted material to achieve molecular and crystallite orientation. BMG's material demonstrated a significant reduction in pin-on-disk wear, but the reduction was not as significant as with highly cross-linked versions of UHMWPE (Oka, M. et al., "Wear-resistant properties of newly improved UHMWPE," Trans. $5^{th}$ World Biomaterials Congress, 520, 1966).

Importantly, for these methods, thermal annealing of the polymer during or after irradiation causes the free radicals (generated during irradiation) to recombine and/or form a more highly cross-linked material. Reducing or quenching free radicals is extremely important because a lack of free radicals can prevent significant UHMWPE aging.

B. Chemical Cross-Linking

Like irradiation cross-linking, chemical cross-linking of UHMWPE has been investigated as a method for increasing wear resistance. Chemical cross-linking provides the benefit of cross-linking while avoiding the degradative effects of ionizing irradiation.

The Orthopaedic Hospital/University of Southern California has submitted patent applications for cross-linking UHMWPE in order to increase wear resistance in orthopaedics (European Patent Application EP 0722973 A1), including a method wherein the cross-linking results in a material with a decreased crystallinity. Cross-linking is accomplished by irradiation in a molten state or photo cross-linking in a molten state, or cross-linking with a free radical generating chemical, and annealing the cross-linked polymer to pre-shrink it. Residuals from the chemical cross-linking reaction, however, are a regulatory concern and may contribute to long-term oxidative degradation.

It remains an object of the present invention, therefore, to provide a process for treating UHMWPE for use in orthopaedic implants such that the long-term wear properties of the UHMWPE are improved.

It is another object of the present invention to provide a process for treating UHMWPE for use in orthopaedic implants in vivo such that problems with the implants in situ are eliminated.

It is a further object of the present invention to provide a process for treating high energy beam irradiated UHMWPE so as to reduce or quench free radical concentration.

It is a further object of the present invention to provide a process for treating high energy beam irradiated UHMWPE with electromagnetic energy for reducing or quenching free radical concentration and promoting formation of cross-links.

It is a further object of the present invention to provide a process for treating high beam energy irradiated UHMWPE with mechanical wave energy for reducing or quenching free radical concentration and promoting formation of cross-links.

BRIEF SUMMARY OF THE INVENTION

The present invention provides a process to reduce or quench free radical concentration in irradiation cross-linked UHMWPE. More specifically, the present invention utilizes electromagnetic or mechanical wave energy to rapidly and efficiently promote free radical combination and formation of cross-links in irradiated UHMWPE. In a first embodiment, free radical concentration is reduced or quenched by irradiating cross-linked UHMWPE with pure or intense infrared radiation. Treatment with infrared radiation may be performed under vacuum. Following irradiation, the UHMWPE is allowed to cool ideally in the presence of an inert gas. In a second embodiment, free radical concentration is reduced or quenched by exposing irradiated UHMWPE to mechanical wave energy, such as ultrasound.

In summary, the process of treating irradiated cross-linked UHMWPE with electromagnetic or mechanical wave energy provides a rapid and efficient method for reducing or quenching radical concentration. Furthermore, UHMWPE having a reduced free radical concentration is more resistant to long-term oxidative degradation, and is, therefore, more suitable for use in prosthetic implants.

DETAILED DESCRIPTION OF THE PREFERRED EMBODIMENT

Figure 1:
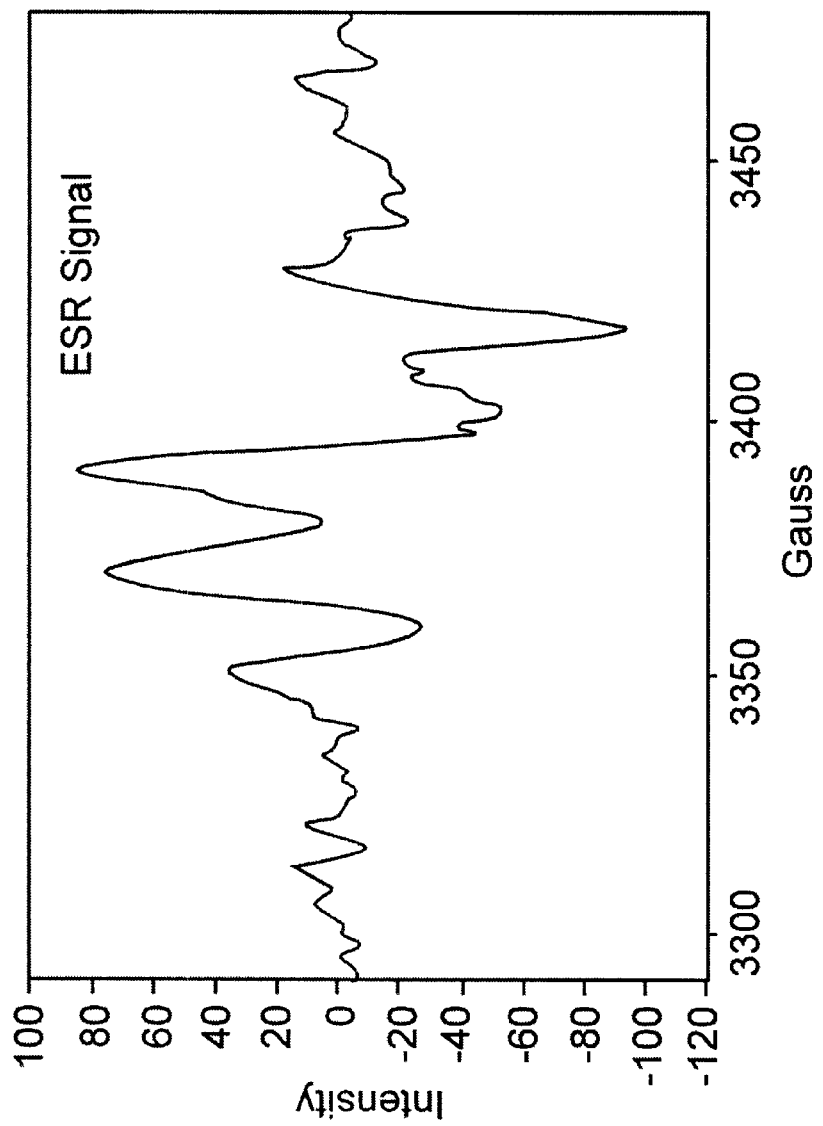
FIG. 1 shows a typical ESR spectrum of 100 kGy irradiated UHMWPE.

Exposure of UHMWPE to high energy beam radiation results in the cleavage of carbon-carbon and carbon-hydrogen bonds within the polyethylene chains. Such high energy beam radiation includes gamma, electron beam, or x-ray radiation. Cleavage of these bonds can cause various chemical reactions and/or interactions to occur which alter the physical and chemical characteristics of the UHMWPE polymer. One of these reactions is the formation of free radicals. Formation of free radicals during irradiation primarily include a combination of alkyl and allyl type free radicals. In the presence of oxygen, however, a small fraction of peroxy radicals are also formed. To reduce the formation of peroxy radicals, the presently disclosed process is performed under vacuum or in the presence of an inert gas, such as argon, although this is not essential.

Although it has been shown that cross-linking is the predominant reaction occurring immediately after high energy beam irradiation, free radicals formed during irradiation can exist indefinitely. Furthermore, reactive intermediates are continuously formed and decayed. Exposure of free radicals to molecular oxygen or any other reactive oxidizing agent can result in their oxidation. Oxidation typically results in a cascade of deleterious physical changes such as reductions in structural and wear properties of the UHMWPE polymer. Because cross-linking has been shown to have beneficial effects on UHMWPE wear resistance, it is desired to prepare a UHMWPE with a greater number of cross-links with a reduced or quenched free radical concentration. The presently disclosed process is operable to eliminate or quench free radicals concentration thereby reducing oxidative degradation (or aging) of UHMWPE over time.

All previous efforts to increase the rate of free radical recombination before oxidation occurs have used heating treatments, above or below UHMWPE melting point. These techniques-are time consuming due to the required melting time, and subsequent cooling time. More particularly, melting UHMWPE is generally performed with a conventional oven. As demonstrated below, melting UHMWPE using a conventional convection oven requires an extended period of time as compared to pure infrared radiation. Next, oven melted UHMWPE is allowed to cool within the oven, and ideally under vacuum or in an inert environment to prevent oxidation of the UHMWPE by molecular oxygen. Thus, UHMWPE cooling occurs slowly because of heat radiating from the "hot walls" of the oven. In contrast, infrared heating provides: (1) high heat fluxes resulting in heating rates up to 200° C./s (materials dependent) due to the fact that only the sample is heated to the desired temperature, (2) heating only to the part (i.e. low thermal mass) through direct resonation of molecular bonds in polymer chains, (3) fast cooling rates due to the "cold wall" nature of the process in which only the sample is heated, and (4) a precise process, which is essentially shape independent when utilizing proper furnace designs. Thus, using intense infrared radiation to heat, and thereby melt irradiated UHMWPE to quench free radical concentrations occurs more rapidly and efficiently than is available with a conventional vacuum oven.

In a second embodiment, mechanical wave energy is used to promote free radical combination thereby forming cross-links. As disclosed with infrared radiation treatment, mechanical wave energy stimulates molecular vibration to accelerate recombination of free radicals. In so doing, it also provides a more rapid quenching of free radicals than conventional oven heating.

The following examples are provided to explain and describe the invention in more detail. The examples, however, are not to be construed as limiting the scope of the invention, but are provided to enable those skilled in the art to practice the invention as claimed.

EXAMPLE 1

Use of Above Melting Infrared Radiation Heating to Reduce Free Radicals in Irradiated UHMWPE.

A Ram extruded 6.35 cm diameter GUR 1050 UHMWPE bar stock (manufactured by Poly Hi Solidur, Fort Wayne, Ind.) was irradiated to a dose of 100±8 kGy. Following irradiation, a 2.5 cm thick specimen of irradiated UHMWPE was prepared with a thermocouple centrally positioned within the core of specimen. Next, the specimen was placed within a 27-kW radial infrared heating system consisting of a Yokogawa controller. The infrared heating system was equipped with a 10.2 cm (4 in.) diameter quartz chamber, and 22 active tubular quartz tungsten halogen filaments arranged circumferentially around the quartz chamber. Each tungsten filament being rated at 1300 W, and 16.5 cm (6.5in.) in length.

Within the chamber, the irradiated UHMWPE specimen was exposed to several vacuum/argon purge cycles. A vacuum of 100 millitorr was then applied. The tubular quartz tungsten halogen filaments were activated to completely melt by infrared radiation the UHMWPE. During the process of melting, the surface temperature of the specimen was regulated so as to not exceed 250° C. Under these conditions, melting of the specimen required 45 minutes of exposure to the infrared radiation. After the specimen was completely melted, infrared radiation was applied for an additional 15 minutes. After the additional 15 minutes of treatment with infrared radiation, the melted UHMWPE was allowed to cool under an argon purge to about 50° C. (approximately 3 hours). The UHMWPE specimen was then removed from the infrared heating system and allowed to cool to room temperature.

For comparative purposes, a separate 2.5 cm thick specimen of 100±8 kGy irradiated UHMWPE was heated to 160° C. in a Fisher Scientific model 282A vacuum oven. During the heating process, the specimen was exposed to a vacuum of approximately 25 torr (0.98 in Hg). Under these conditions, complete melting was achieved after 5.5 hours. Once complete melting was achieved, the specimen was cooled to room temperature under a nitrogen purge (approximately 12 hours). Furthermore, an untreated control gamma irradiated specimen was included for comparison.

Figure 2:
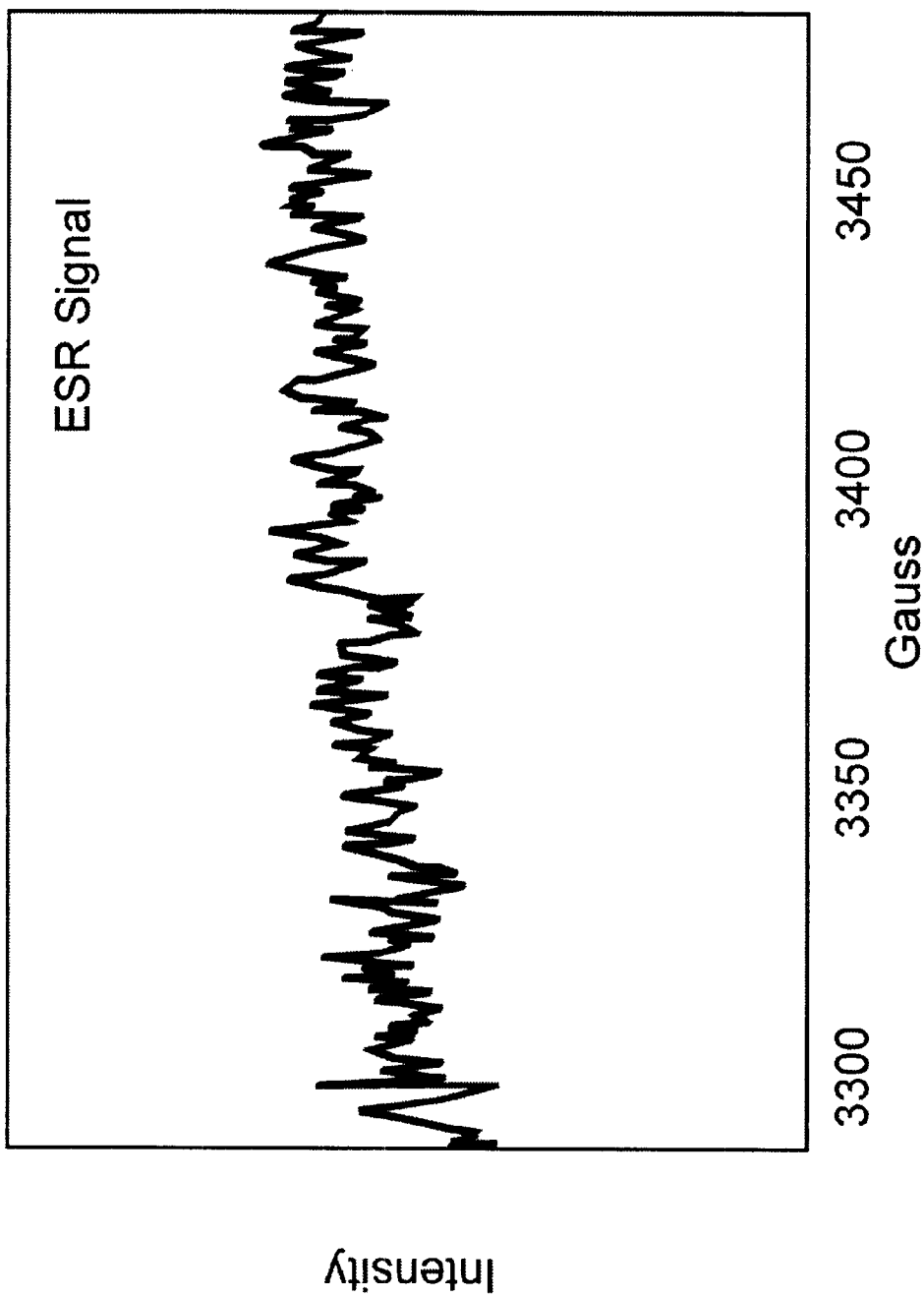
FIG. 2 shows a typical ESR spectrum of 100 kGy irradiated UHMWPE remelted using a conventional oven.
Figure 3:
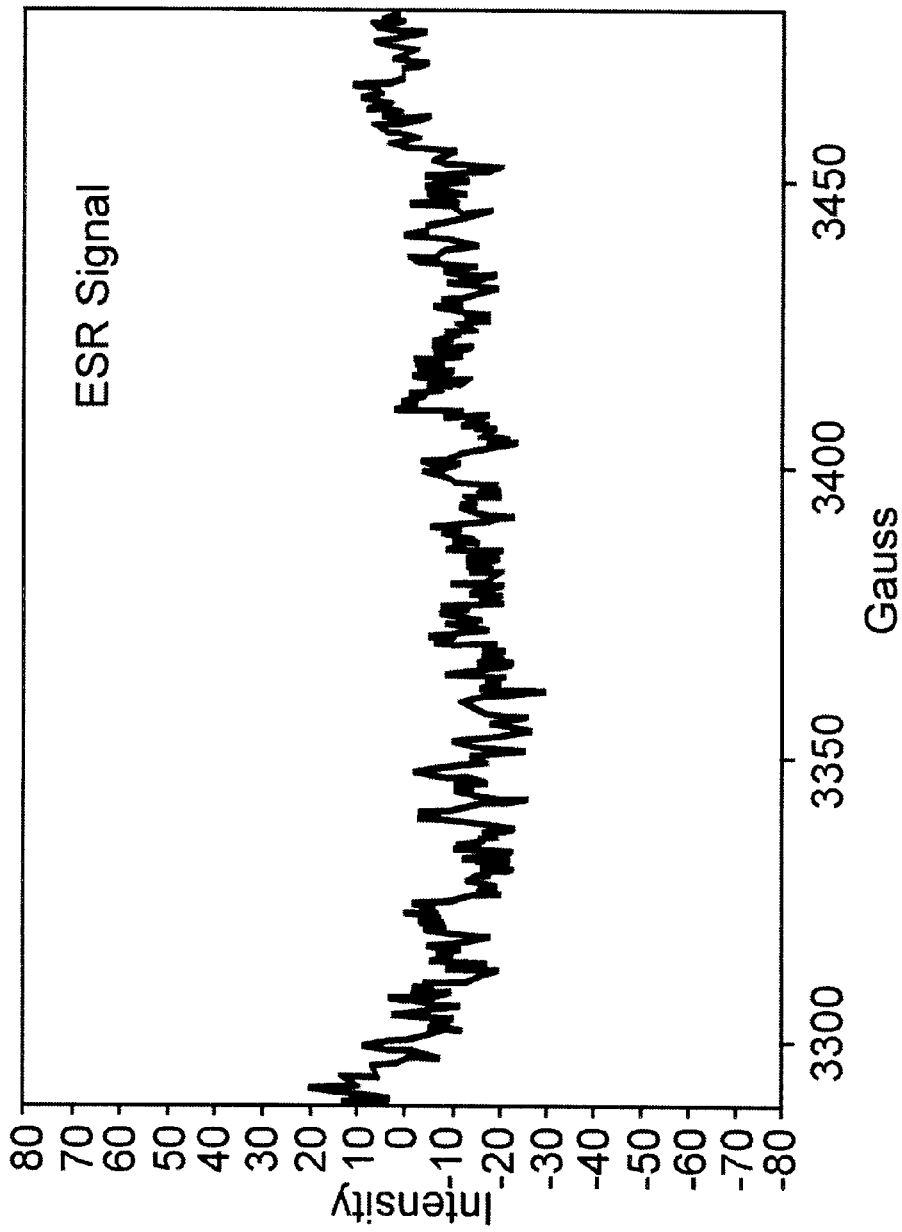
FIG. 3 shows a typical ESR spectrum of 100 kGy irradiated UHMWPE remelted using infrared radiation.

Electron spin resonance spectroscopy (ESR) was performed to determine whether near infrared treatment of irradiated UHMWPE quenched free radical concentration. Samples analyzed included untreated gamma irradiated UHMWPE, oven melted gamma irradiated UHMWPE, and infrared treated gamma irradiated UHMWPE. Five (5) replicates having a 3.7 mm diameter and 10 mm total length were prepared from each test specimen, and subjected to ESR analysis using a X-band ESR spectrophotometer operating at a microwave frequency of 10 GHz with a rectangular $TE_{,102}$ cavity (Bruker). After scanning each specimen, the absolute magnitude of free radical concentration was computed by comparing the area of absorption curve of a test sample with that of NIST intensity standard SRM-2601. Typical ESR spectra for each sample are illustrated in FIGS. 1 through 3.

The results of the ESR analysis for control, oven remelted, and infrared remelted 100 kGy irradiated UHMWPE samples are shown in Table 1. Free radical concentration for these samples is provided as spins/gram.

EXAMPLE 2
Use of Sub-melting Infrared Radiation Heating to Reduce Free Radicals in Gamma Irradiated UHMWPE.

Figure 4:
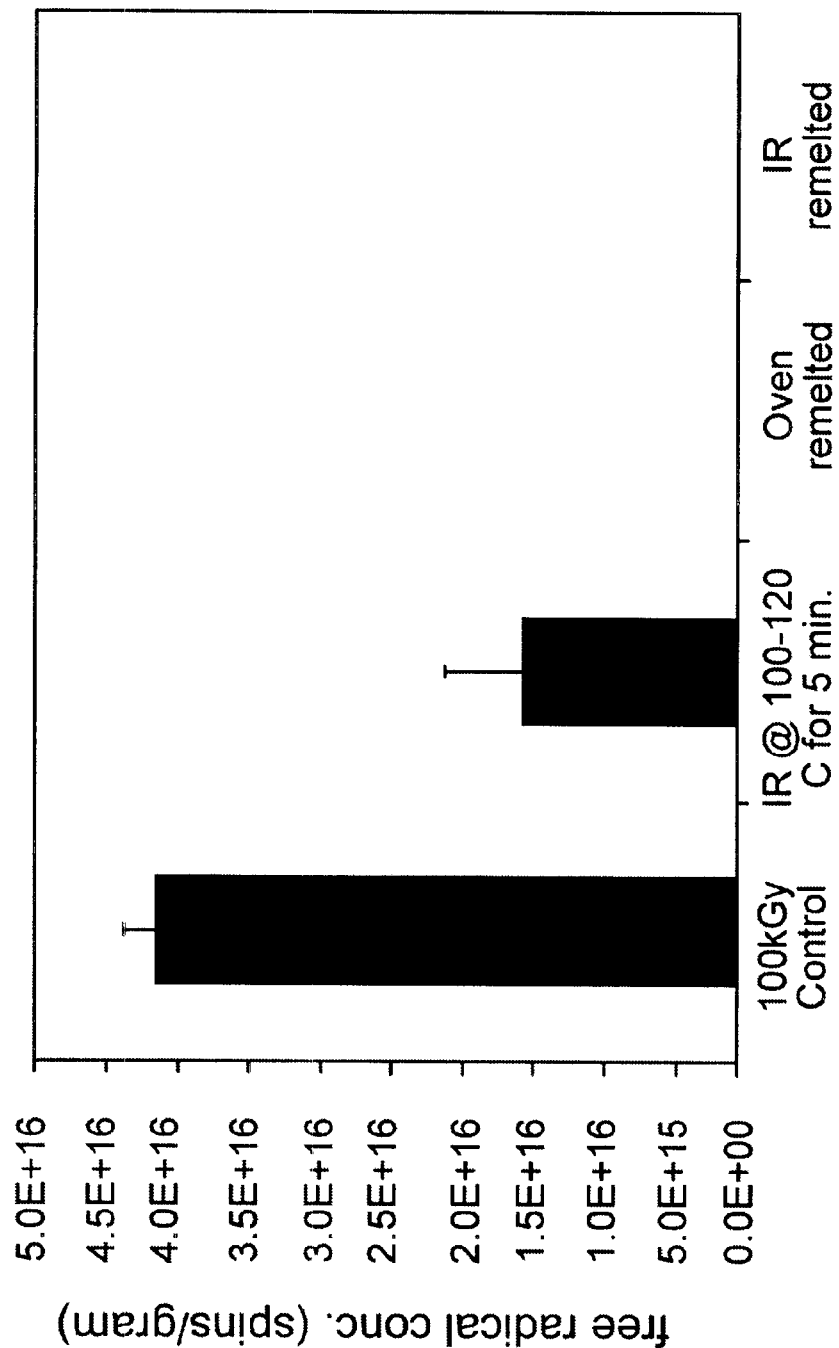
FIG. 4 shows average free radical concentrations (spins/gm) for untreated and infrared treated 100 kGy irradiated UHMWPE bar stock.

Ram extruded 6.35 cm diameter GUR 1050 UHMWPE bar stock was irradiated to a dose of 100±8 kGy. A 2.5 cm thick specimen with a thermocouple placed in the core was placed in a radial infrared heating system consisting of a 10.2 cm diameter quartz vacuum chamber with three 16.5 cm long, 1300 W active tubular quartz tungsten halogen filaments. The filaments were arranged circumferentially around the outside of the chamber. After several vacuum/argon purge cycles, a vacuum of 100 millitorr was applied and the bar was heated to between 100 and 120° C. by varying the percentage of rated voltage of the lamps. The bar was held at that temperature for 5 minutes before turning off the lamps and allowing cooling to 50 ° C under an argon purge, which took approximately 1 hour. It was observed that the sub-melting infrared radiation treatment of gamma irradiated UHMWPE significantly reduced the concentration of free radicals ($p=1.9 \times 10^4$) in comparison to the untreated irradiated control, however, a considerable number of free radicals remained. The oven melted specimen contained no free radicals. Average free radical concentrations for each sample are illustrated in FIG. 4.

EXAMPLE 3
Use of Ultrasound to Reduce Free Radicals in Irradiated UHMWPE.

Figure 5:
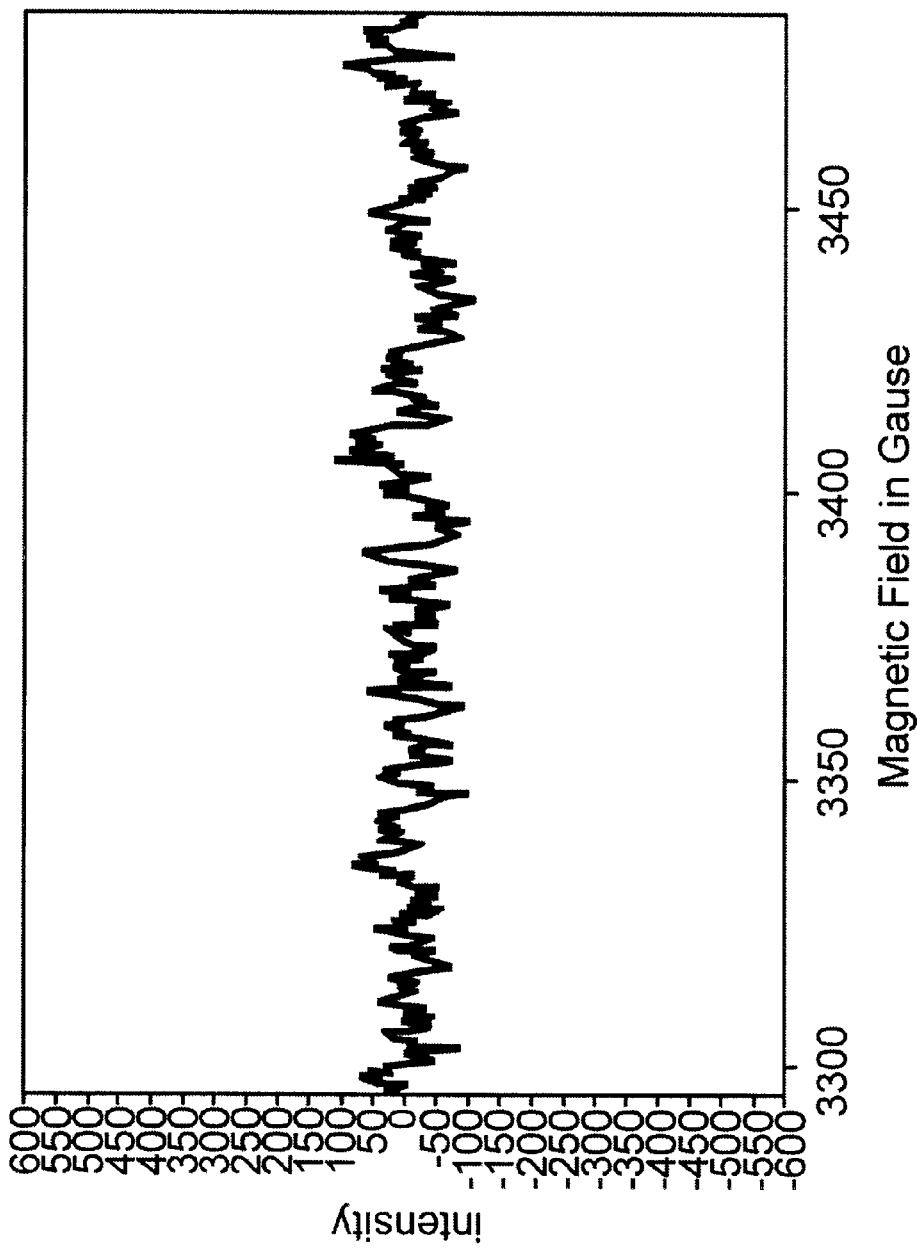
FIG. 5 shows a typical ESR spectrum of 100 kGy irradiated UHMWPE treated with ultrasound for approximately 5 seconds.

A 6.36 cm diameter, 3.3 mm (0.13 in) thick disk specimen, was taken from the identical 100±8 kGy irradiated GUR 1050 UHMWPE bar stock material described in Example 1. The specimen was cut in half and placed under a 45 cm×35 cm horn of a 1 kW 20 kHz Branson ultrasonic welding press. At a pressure of 496 kPa (72 psi), ultrasonic wave energy was applied at an amplitude of approximately 50 $\mu$M for approximately 5 seconds. During the exposure to ultrasound, the edge of the UHMWPE specimen became translucent (melted). ESR analysis was performed on samples taken from unmelted portions of the irradiated UHMWPE. A typical ESR spectrum for irradiated UHMWPE treated with ultrasound is shown in FIG. 5 with data summarized in Table I. As FIG. 5 illustrates, free radicals were not detected in ultrasound treated irradiated UHMWPE.

EXAMPLE 4
Use of Ultrasound to Reduce Free Radicals in Gamma Irradiated UHMWPE.

Figure 6:
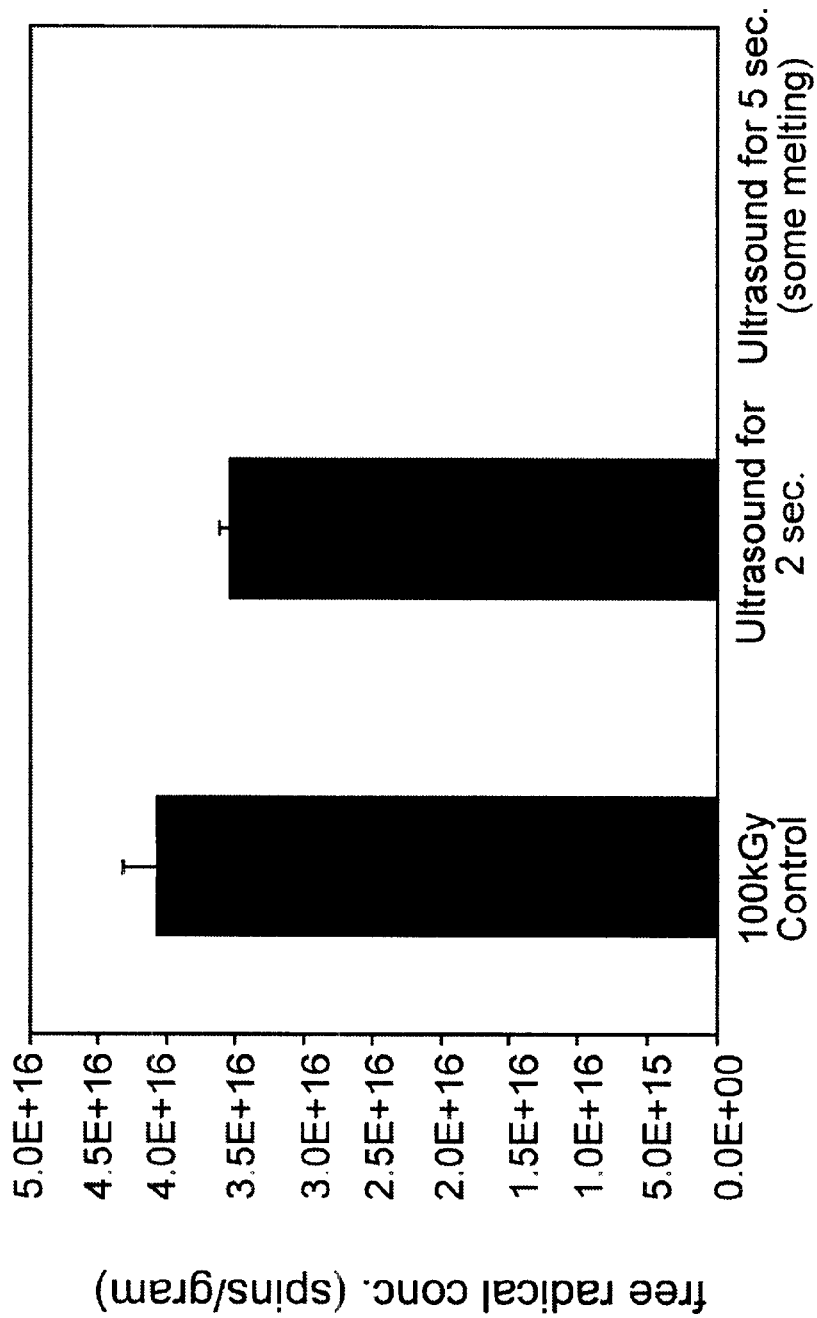
FIG. 6 shows average free radical concentrations (spins/gm) for untreated and ultrasound treated 100 kGy irradiated UHMWPE bar stock.

Ram extruded 6.36 cm diameter GUR 1050 UHMWPE bar stock was irradiated to a dose of 100±8 kGy (same source as Example 2). Using a 2 kW 20 kHz Dukane ultrasonic welding press having a 2.25 diameter high gain horn, a 7.0 mm thick disk was subjected to an amplitude of 63.5 $\mu$m and a frequency of 20 kHz for 2 seconds. As with the above examples, five (5) replicates were evaluated using ESR. For comparison, an untreated 100 kGy irradiated specimen, which had gone through all of the same processes as the treated specimen except for the ultrasound exposure, was also sampled and analyzed using ESR. The free radical concentration for each of the 5 samples of the 2 specimens is summarized in Table I and illustrated along with the average for the untreated control in FIG. 6. Although free radicals were detected in the specimen (average of $3.5 \times 10^{16}$ spins/gram), the number was significantly less than the untreated control (p=0.0017).

TABLE I

ESR data for control 100 kGy irradiated UHMWPE samples and infrared and ultrasound treated samples.

| Specimen | Sample | Spins | Average | Std. Dev. |
|---|---|---|---|---|
| 100 kGy control | 1 | 4.36E + 16 | 4.09E + 16 | 2.20E + 15 |
|  | 2 | 4.03E + 16 |  |  |
|  | 3 | 3.77E + 16 |  |  |
|  | 4 | 4.07E + 16 |  |  |
|  | 5 | 4.21E + 16 |  |  |
| Oven remelted | 1 | 0 | 0 | 0 |
|  | 2 | 0 |  |  |
|  | 3 | 0 |  |  |
|  | 4 | 0 |  |  |
|  | 5 | 0 |  |  |
| IR @ 100–120 C. for 5 min. | 1 | 6.80E + 15 | 1.51E + 16 | 5.46E + 15 |
|  | 2 | 2.18E + 16 |  |  |
|  | 3 | 1.48E + 16 |  |  |

TABLE I-continued

ESR data for control 100 kGy irradiated UHMWPE samples and infrared and ultrasound treated samples.

| Specimen | Sample | Spins | Average | Std. Dev. |
|---|---|---|---|---|
| | 4 | 1.74E + 16 | | |
| | 5 | 1.45E + 16 | | |
| IR remelted | 1 | 0 | 0 | 0 |
| | 2 | 0 | | |
| | 3 | 0 | | |
| | 4 | 0 | | |
| Ultrasound for 2 sec. (Dukane) | 1 | 3.64E + 16 | 3.5E + 16 | 1.7906E + 15 |
| | 2 | 3.38E + 16 | | |
| | 3 | 3.14E + 16 | | |
| | 4 | 3.55E + 16 | | |
| | 5 | 3.52E + 16 | | |
| Ultrasound for 5 sec. (Branson) | 1 | 0 | 0 | 0 |
| | 2 | 0 | | |
| | 3 | 0 | | |
| | 4 | 0 | | |
| | 5 | 0 | | |

While in accordance with the patent statutes, a best mode and a preferred embodiment has been set forth, the scope of the invention is not limited thereto, but rather by the scope of the attached claims.

What is claimed is:

1. A process for quenching free radicals in an irradiated ultra high molecular weight polyethylene (UHMWPE) preform used as an orthopedic component, said process comprises:
    exposing said UHMWPE preform with pure or intense infrared radiation to promote recombination of said residual free radicals in said UHMWPE;
    controlling surface temperature of said UHMWPE preform during said irradiation so as to prevent degradation of said UHMWPE; and,
    cooling said UHMWPE preform to room temperature.

2. The process claimed in claim 1, wherein said UHMWPE is exposed to a vacuum during said radiation.

3. The process claimed in claim 1, wherein said cooling step is in the presence of an inert gas.

4. The process claimed in claim 1, wherein said controlling step includes maintaining the surface temperature of said UHMWPE below about 300° Celsius.

5. The process of claim 1, wherein sad exposing step includes a tubular quartz tungsten filament lamp as the source of said intense infrared radiation.

6. The process claimed in claim 3, wherein said inert gas used in said cooling step is selected from the group consisting of argon and nitrogen.

7. A process for treating an irradiated UHMWPE preform used as an orthopedic component, said process comprises:
    exposing said UHMWPE to ultrasonic wave energy to quench free radicals in said irradiated UHMWPE.

8. A process for quenching free radicals in an irradiated UHMWPE preform used as an orthopedic component, said process comprises:
    exposing said UHMWPE with pure or intense infrared radiation to promote recombination of said free radicals in said UHMWPE; and
    cooling said UHMWPE to room temperature.

9. The process claimed in claim 8 wherein said UHMWPE is exposed to a vacuum during said radiation.

10. A process of quenching free radicals in an irradiated UHMWPE preform used as an orthopedic component, said process comprises:
    applying an energy to effect resonation of a molecular bond in said irradiated UHMWPE.

11. The process of claim 10, wherein said energy is pure or intense infrared radiation.

12. The process of claim 10, wherein said energy is ultrasonic wave energy.

* * * * *